(12) United States Patent
Mifune et al.

(10) Patent No.: US 7,080,025 B2
(45) Date of Patent: Jul. 18, 2006

(54) SYSTEM AND METHOD FOR SCHEDULING MEDICAL EXAMINATIONS UTILIZING QUEUES AND PROVIDING MEDICAL EXAMINATION ROUTE GUIDE INFORMATION TO THE SCHEDULED EXAMINATIONS

(75) Inventors: Yoshiteru Mifune, Hirakata (JP); Naoyuki Ito, Katano (JP)

(73) Assignee: Matsushita Electric Industrial Co., Ltd., Kadoma (JP)

( * ) Notice: Subject to any disclaimer, the term of this patent is extended or adjusted under 35 U.S.C. 154(b) by 1043 days.

(21) Appl. No.: 09/898,463

(22) Filed: Jul. 5, 2001

(65) Prior Publication Data

US 2002/0152107 A1 Oct. 17, 2002

(30) Foreign Application Priority Data

Apr. 11, 2001 (JP) ............................. 2001-112387

(51) Int. Cl.
*G06F 9/46* (2006.01)

(52) U.S. Cl. ....................................................... 705/9

(58) Field of Classification Search ................ 705/9
See application file for complete search history.

(56) References Cited

U.S. PATENT DOCUMENTS

| | | | | |
|---|---|---|---|---|
| 4,937,743 A | * | 6/1990 | Rassman et al. ............... 705/8 |
| 5,006,983 A | * | 4/1991 | Wayne et al. .................. 705/8 |
| 5,032,083 A | * | 7/1991 | Friedman .................... 434/112 |
| 5,065,315 A | * | 11/1991 | Garcia ........................... 705/2 |
| 5,502,806 A | * | 3/1996 | Mahoney et al. ........... 715/839 |
| 5,541,845 A | * | 7/1996 | Klein ......................... 701/247 |
| 5,559,707 A | * | 9/1996 | DeLorme et al. ........... 701/200 |
| 5,642,303 A | * | 6/1997 | Small et al. ................ 708/109 |
| 5,692,125 A | * | 11/1997 | Schloss et al. ................. 705/9 |
| 5,790,974 A | * | 8/1998 | Tognazzini ............... 455/456.5 |
| 5,831,534 A | * | 11/1998 | Mooney et al. .......... 340/573.1 |
| 5,912,630 A | * | 6/1999 | McCullough et al. ........ 340/3.7 |
| 5,924,075 A | * | 7/1999 | Kanemitsu ..................... 705/6 |
| 5,938,721 A | * | 8/1999 | Dussell et al. .............. 701/211 |
| 5,963,948 A | * | 10/1999 | Shilcrat ...................... 707/100 |
| 5,987,421 A | * | 11/1999 | Chuang .......................... 705/7 |
| 5,991,730 A | * | 11/1999 | Lubin et al. .................... 705/3 |
| 6,179,358 B1 | * | 1/2001 | Hirayama et al. ....... 296/24.38 |
| 6,329,919 B1 | * | 12/2001 | Boies et al. ............. 340/573.1 |
| 6,345,260 B1 | * | 2/2002 | Cummings et al. ............ 705/8 |

(Continued)

FOREIGN PATENT DOCUMENTS

GB 2315350 A * 1/1998

(Continued)

OTHER PUBLICATIONS

House Call Journal—Today Show Picks Call Doc☐☐Call Doc Medical Group, vol. 2, No. 1, Aug. 1998.*

(Continued)

*Primary Examiner*—Tariq R. Hafiz
*Assistant Examiner*—Scott L. Jarrett
(74) *Attorney, Agent, or Firm*—Smith Patent Office

(57) ABSTRACT

In an on-site medical examination, an appointment is made from a work office in order to shorten the entire medical examination time of the patients and the order and the route can be shown at the medical examination site. The scheduler includes a waiting queue for individual medical examination items and a waiting queue for individual patients. The efficiency of the medical examination is achieved by communicating by wireless displays carried by patients at the medical examination site and by giving individual guidance concerning the places to go at the site.

6 Claims, 11 Drawing Sheets

U.S. PATENT DOCUMENTS

| | | | |
|---|---|---|---|
| 6,389,454 B1 * | 5/2002 | Ralston et al. | 709/204 |
| 6,411,899 B1 * | 6/2002 | Dussell et al. | 701/211 |
| 6,421,649 B1 * | 7/2002 | Rattner | 705/2 |
| 6,678,613 B1 * | 1/2004 | Andrews et al. | 701/213 |
| 6,748,364 B1 * | 6/2004 | Waytena et al. | 705/5 |
| 2002/0059082 A1 * | 5/2002 | Moczygemba | 705/3 |
| 2005/0060198 A1 * | 3/2005 | Bayne | 705/2 |

FOREIGN PATENT DOCUMENTS

| | | | |
|---|---|---|---|
| JP | 8-194853 A | | 7/1996 |
| JP | 10161193 | * | 6/1998 |
| JP | 11-205337 A | | 7/1999 |
| JP | 200263676 | * | 8/2000 |
| JP | 2002-74121 | * | 3/2002 |
| JP | 2002-329002 | * | 11/2002 |
| JP | 2003-30416 | * | 1/2003 |
| JP | 2004-110238 | * | 4/2004 |
| WO | WO 9725682 | * | 7/1997 |
| WO | WO200186481 A2 * | | 5/2000 |
| WO | WO 0104577 A1 * | | 1/2001 |

OTHER PUBLICATIONS

Katz, Jesse H., Simulation of Outpatient Appointment Systems Communications of the ACM, Apr. 1969, vol. 12, No. 4, pp. 215-222.*

Dowd, Gregory et al., CyberGuide: A mobile context-aware tour guide Wireless Networks, 1997, vol. 3, pp. 421-433.*

Cheverst, Keith et al., Experiences of Developing and Deploying a Context-Aware Tourist Guide: The GUIDE Project ACM, 2000.*

Ancona, M. et al., Mobile Computer in a hospital: the WARD-IN-HAND project ACM SAC 2000, Mar. 2000.*

Rosen, Jack, IMprove Managed Care Services and the Bottom Line Health Management Technology, Nov. 2000, vol. 21, No. 11, p. 54.*

Butz, Andreas et al., A Hybrid Indoor Navigation System ACM 2001.*

* cited by examiner

SYSTEM AND METHOD FOR SCHEDULING MEDICAL EXAMINATIONS UTILIZING QUEUES AND PROVIDING MEDICAL EXAMINATION ROUTE GUIDE INFORMATION TO THE SCHEDULED EXAMINATIONS

BACKGROUND OF THE INVENTION

1. Field of the Invention

The present invention relates to a medical examination system that manages the order of patients waiting for a medical examination so as to minimize the time that is required from the start to the end of the medical examination of the patients in an on-site medical examination.

2. Discussion of the Related Art

In a conventional medical examination system, the system controls the order of patients waiting for a medical examination. Systems or algorithms which control waiting lines, under the presupposition that patients have already arrived at a fixed institution for a medical examination have been proposed. In these systems or algorithms, the order is set so as to optimize the order of later arriving patients waiting in line (Japanese Unexamined Patent Publication No. Hei 08-194853) or the order is indicated (Japanese Unexamined Patent Publication No. Hei 11-205337). These medical examination systems have configurations that cannot, as a whole, be physically moved.

Accordingly, as in the case where the patients are presupposed to receive a medical examination during working hours in a working office or during farm work, an appointment that makes the amount of time of work interruption the shortest cannot be achieved by minimizing the time from the start to the end of the medical examination that is required for individual patients, even if the starting time of the examination is delayed. In addition, in an on-site medical examination the portability of the entire system is required places, layouts and the order for the medical examination cannot be set because of installment conditions in working offices or local public offices where the medical examination is held. Accordingly, guidance for the order and places of medical examination that is required based on appointment conditions cannot be given to individual patients at the site of the medical examination.

Therefore, in conventional on-site medical examinations, these conventional systems for controlling waiting time have not been utilized because an appointment cannot be made for the shortest medical examination time by grasping the medical examination condition during working hours and also there is no portability nor is there guidance given to individual patients at the site. In most on-site medical examinations, an orientation paper including the time precisely arranged schedule according to an individual patient is not delivered in advance. No proper guidance is given at the site concerning the medical examination items or the examination site. Therefore, in many cases, considering the time needed for the actual medical examination, patients waste much time waiting after having arrived at the examination site and, in addition, waste time at a hastily arranged site by being confused concerning the order of the medical examination.

SUMMARY OF THE INVENTION

The purpose of the present invention is to provide a medical examination system that has a simple configuration and has portability. The present invention includes a plurality of wireless display devices that have a display part and a communication part held by each patient waiting for a medical examination.

And in the case of an on-site medical examination under the presupposition that the patients receive a medical examination during working hours, the system makes individual appointments so that the entire medical examination time is minimized by enabling the progress of the medical examination to be understood from the working offices wherein business is carried out and which, even in the case that the place, layout and the order of the medical examination has changed due to the installation conditions of the examination apparatuses, gives guidance concerning the necessary order and the place of the examination based on appointment conditions to individual patients by means of a wireless display device at the site of the medical examination so that the time of interruption of work due to the medical examination is minimized and so that the patients are not confused by the order of the medical examination at an unfamiliar site and can smoothly receive a medical examination.

Thereby, the effects are gained that allocations are sequentially confirmed from the medical examination item that can start the earliest within the range of time for which the allocations are possible and, then, based on the confirmed result the medical examination item which can start the earliest within the range of time where allocations are possible is sequentially confirmed so that the medical examination time for the entirety of the medical examination item is minimized. In addition, the effects are gained that the patients do not waste time, which tends to occur at an on-site medical examination, by being confused at a hastily prepared medical examination site.

DETAILED DESCRIPTION OF THE PREFERRED EMBODIMENTS

Figure 1:
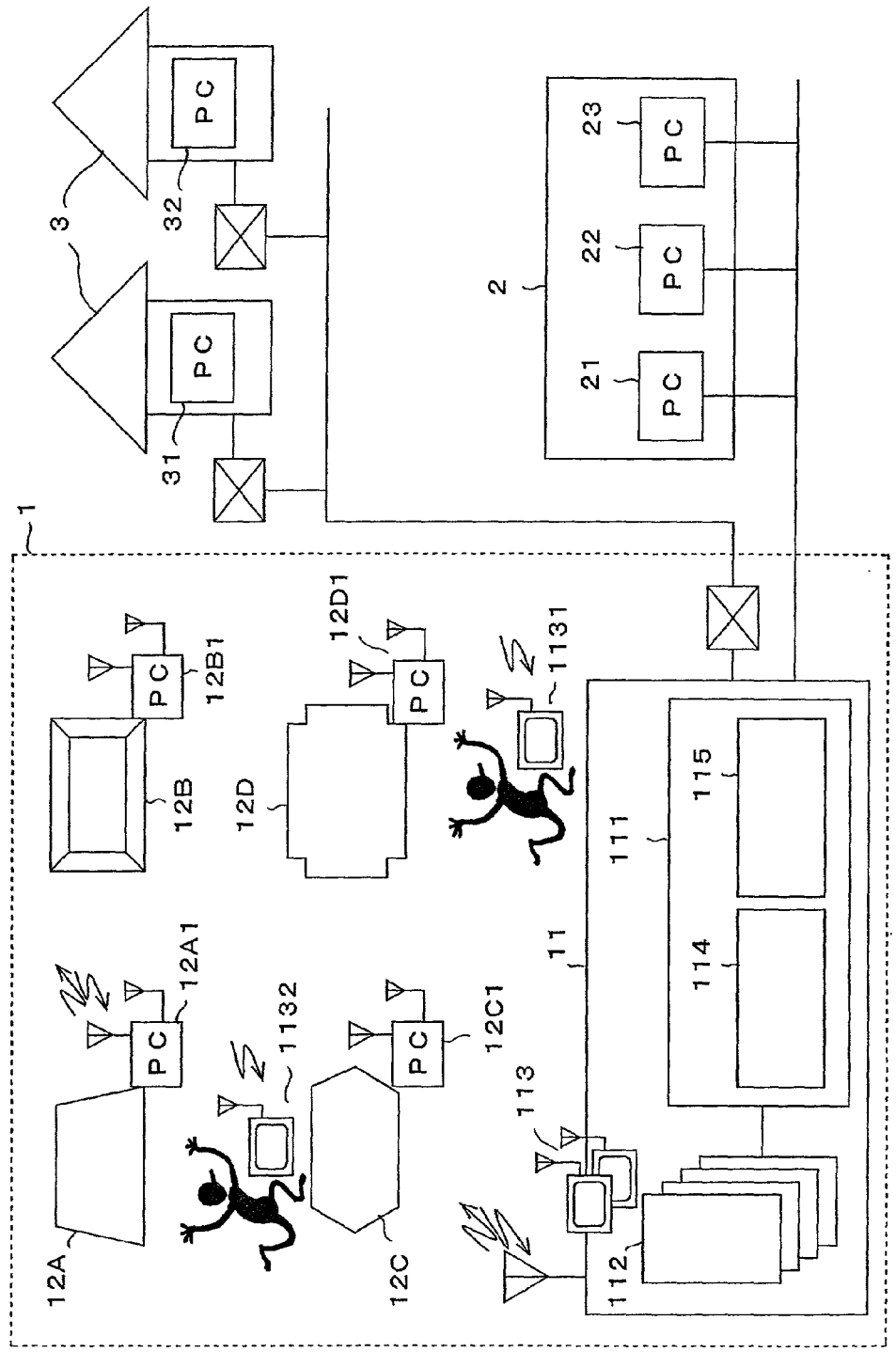
FIG. 1 is a schematic diagram of the entire configuration of a medical examination system according to an embodiment of the present invention.

In the following, an embodiment of the present invention is described in reference to the drawings. First, a conceptual diagram of the entire configuration of a medical examination system according to the present embodiment is described in reference to FIG. 1 so that the entire system can be grasped. FIG. 1 shows an entire site 1 of a medical examination, a server 11, medical examination items 12A to 12D and personal computers (hereinafter referred to as PCs) that have wireless interfaces installed at the site of each of the medical examination items 12A1 to 12D1. The server 11 has a scheduler 111 that includes a waiting queue means 114 for individual medical examination items and a waiting queue means 115 for individual patients and the function of a wireless communication means. A plurality of virtual reality displays 112 form guidance information for receiving the medical examination which mainly include the appointment contents of the scheduler 111. Portable-type wireless display devices 113 correspond to virtual realty displays. The patients go around the medical examination site carrying a wireless display device 1131 or 1132, respectively.

Here, in FIG. 1, an office room 2 is located in a place away from the site 1 of the medical examination where PCs 21, 22 and 23 are personal computers installed within the office room 2. Those PCs 21, 22 and 23 are connected with the server 11 installed at the site 1 of the medical examination via a network so as to have a configuration where the progress of the medical examination can be confirmed or an appointment can be scheduled while staying in the office room 2.

In FIG. 1, in the case that the medical examination is carried out where the site 1 thereof is installed at a local public office, or the like, PCs 31 and 32 installed in each home 3 are connected with the server 11 installed at the site 1 of the medical examination via a network so that the progress of the medical examination can be confirmed and an appointment, can be scheduled while staying at home in the same manner as above.

Figure 2:
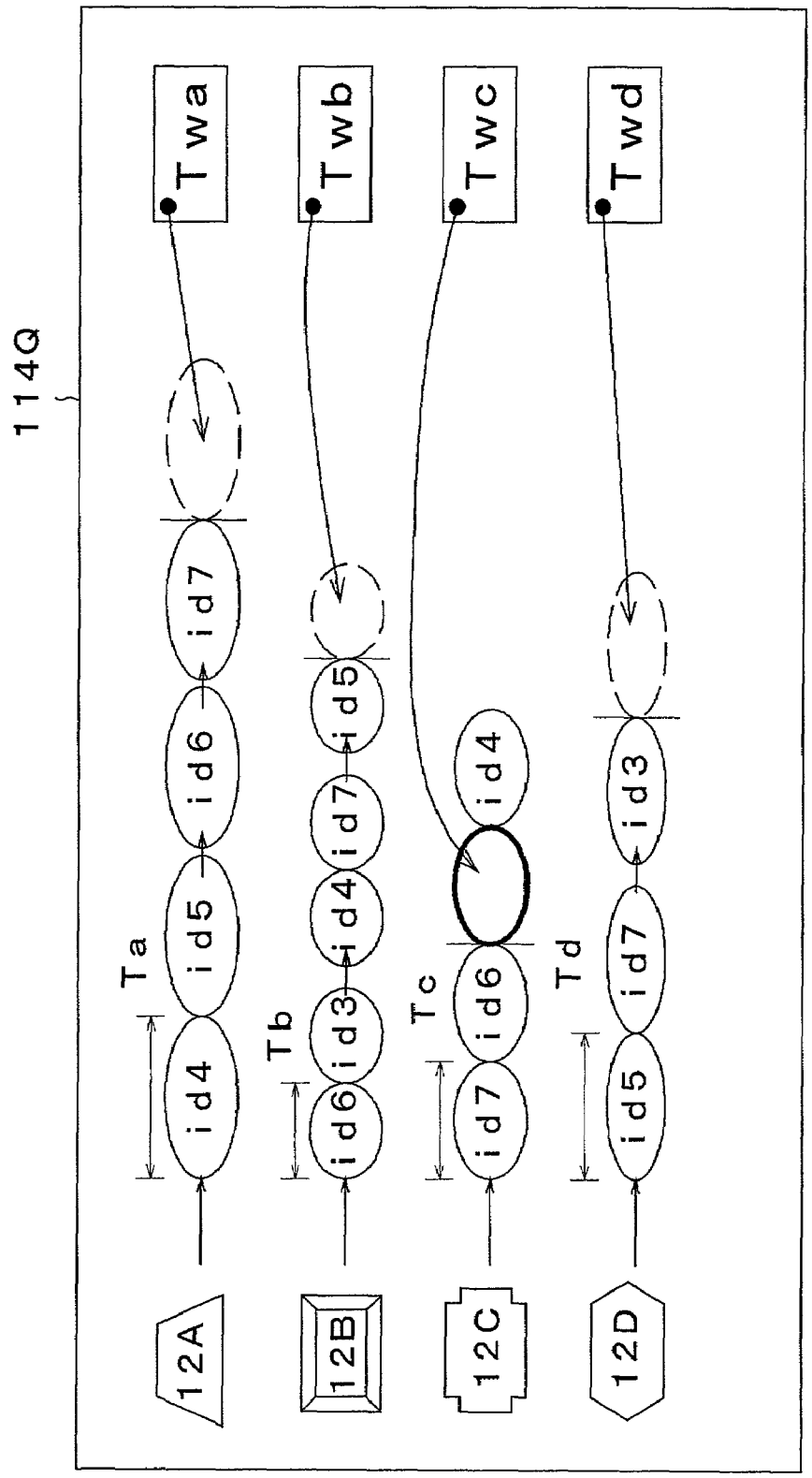
FIG. 2 is a diagram showing a detailed configuration example of a waiting queue means 114 for individual medical examination items of a scheduler 111 shown in FIG. 1.

Next, the configuration of a scheduler of the present embodiment is described in detail. FIG. 2 shows a detailed configuration example of a waiting queue means 114 for individual medical examination items of the scheduler 111 shown in FIG. 1. In FIG. 2, idn (n =3, 4, 5, 6, 7) represents an id for identifying each patient. The waiting queue means 114 for individual medical examination items manages waiting line queue 114Q of the patients for each of the medical examination items 12A to 12D. In addition, the average medical examination times per patient at each of the medical examination items 12A to 12D are denoted as Ta to Td. Twa to Twd represent time periods when the next appointment can be scheduled for each of the medical examination items 12A to 12D, and also represent the time periods of empty queues (hereinafter referred to as an empty id) wherein the first patient is not specified in the waiting queue for individual medical examination items or represents the time period immediately after the completion time of the final patient in the waiting queue means for individual medical examination items, in the case that no empty id exists. In addition, in FIG. 2 arrows between patients id5 and id6 and between patients id6 and id7 of the medical examination item 12A indicate the respective medical examination times are separated from each other and no arrows indicate the continuation of the times. This is the same for the other medical examination items 12B to 12D. In addition, the times available for appointments after the completion of each medical examination are indicated with vertical lines.

Figure 3:
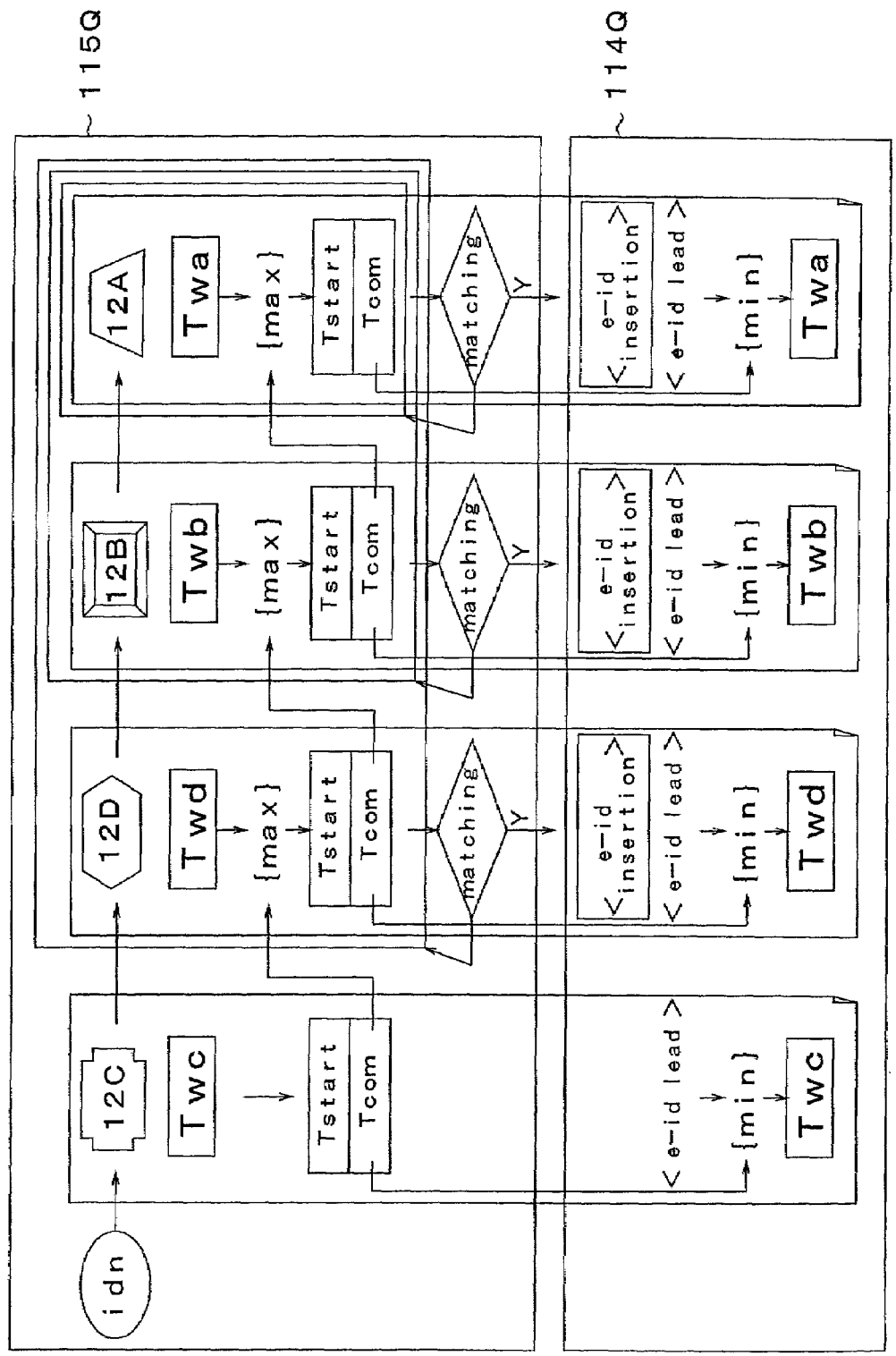
FIG. 3 is a diagram showing a sequence of a detailed appointment process and a configuration example utilizing a waiting queue means 115 for individual patients and a waiting queue means 114 for individual medical examination items by means of the scheduler 111 shown in FIG. 1.

FIG. 3 shows a detailed configuration example in the case that the scheduler 111 shown in FIG. 1 makes an appointment by utilizing the waiting queue means 115 for individual patients and the waiting queue means 114 for individual medical examination items. In FIG. 3 idn represents a new patient who schedules an appointment for a medical examination at this time. The scheduler manages the waiting line queue so that a patient can receive the medical examination in the order starting from the earliest of the times Twa to Twd (Twc<Twd<Twb<Twa) which are possible available for appointment for each medical examination item of the waiting queue 114Q for the medical examination items 12A to 12D shown in FIG. 2. In addition, in FIG. 3 time for the first medical examination appointment item 12C is calculated from the time Twc when the next appointment can be scheduled and the times of the second and subsequent medical examination items are sequentially confirmed by updating times (Twd, Twb, Twa) at which the next appointment can be scheduled under the condition of completion time Tcom of the medical examination item of the previously confirmed stage and by starting from the medical examination item of the earliest time. In FIG. 3, "max" shows a time that is the later of the two inputs while "mm" shows a time that is the earlier of the two inputs. The conditions of the completion time Tcom, and later, of the medical examination item of the previous stage at and after the second item are made to be "matched" in the case that where an appointment is possible. In the case of a match, the appointment is completed where the queue for individual medical examination items is confirmed by means of the queue means 114. In the case that there is not a match, rearrangement is again carried out with a return arrow and the process is repeated until an appointment becomes possible.

In addition, in FIG. 3 in the case that the time confirmed by the appointment process at and after the second item is delayed by the appointment time of the final patient in the original waiting queue for individual medical examination items for integral multiples, or more, of the average medical examination time (Td, Tb, Ta) per patient of each of the medical examination items (12D, 12B, 12A) shown in FIG. 2, one, or a plurality of, empty ids are inserted when an appointment that does not specify a patient of an average medical examination time between, respectively, a waiting time and the starting time of each of the medical examination items (12D, 12B, 12A) is an empty id. This process is shown as "<e-id insertion>." When an appointment for idn at this time is completed, the update of the times Twa to Twd when the next appointment of the waiting queue means 114 is available, including the inserted empty id, is carried out.

Figure 4:
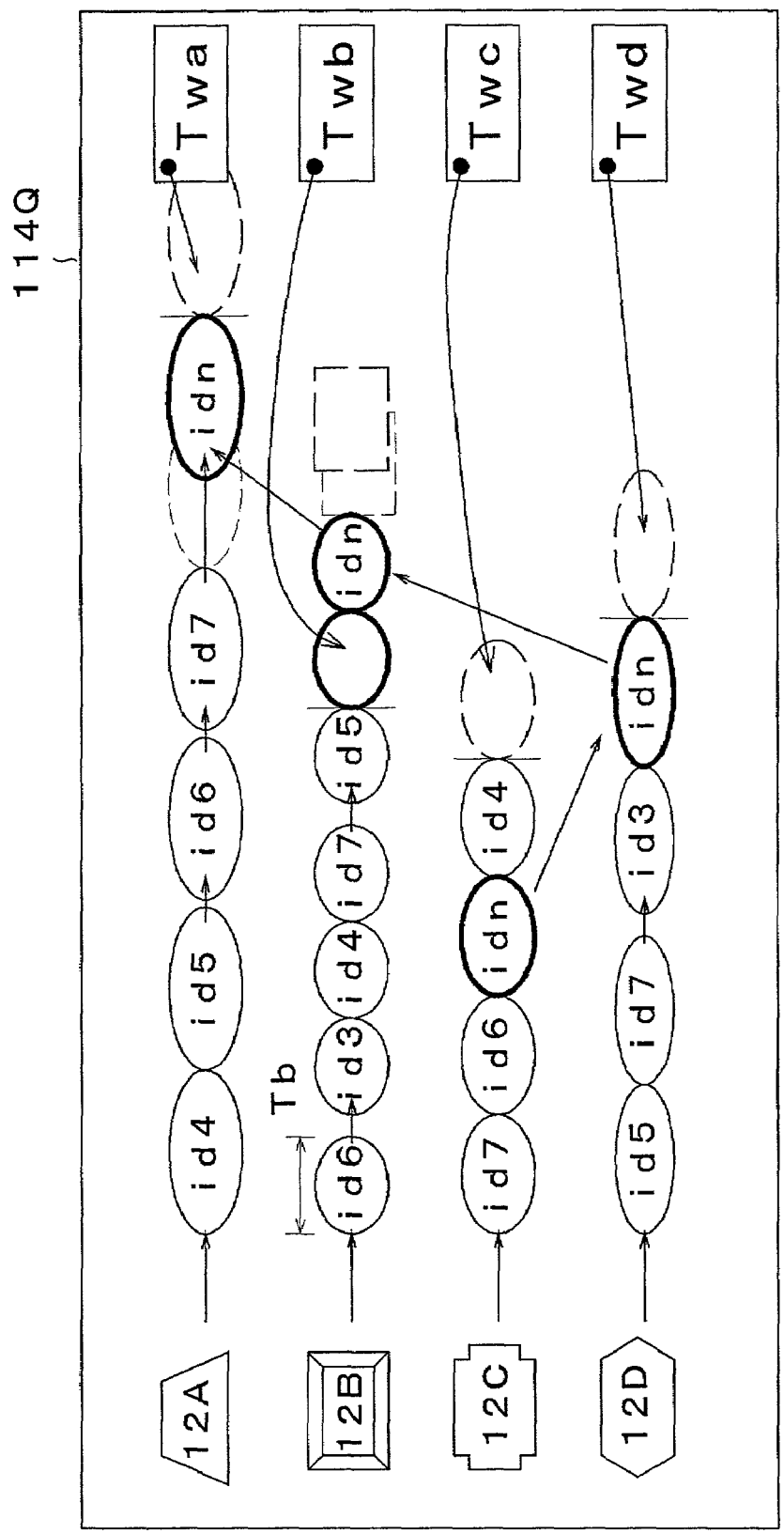
FIG. 4 is a diagram showing an appointment condition of the waiting queue means 114 for medical examination items shown in FIG. 2 after a medical examination appointment of the patient idn shown in FIG. 3 is made.

FIG. 4 shows an appointment condition of the waiting queue 114Q for individual medical examination items shown in FIG. 2 after an appointment is scheduled for a patient idn by the scheduler 111 shown in FIG. 3.

In the appointment process of the patient idn of FIG. 4, since in the original waiting queue 114Q shown in FIG. 2, the sequential order of the time Twa to Twd when the next appointment can be scheduled after each of the medical examination items 12A to 12D is Twc<Twd<Twb<Twa, the first item is confirmed as the medical examination item 12C. Even under the condition after the medical examination completion time of the confirmed medical examination items 12C, the order of the times when the next appointment is available does not change and is the order of Twd<Twb<Twa. Therefore, the second item of the medical examination is confirmed as 12D. The time when the next appointment is possible under the condition after the medical examination completion time of the confirmed medical examination item 12D is the time after the completion time of the final patient id5 of the medical examination item 12B and, therefore, becomes the completion time of 12D and the medical examination item 12A does not have a change and becomes Twb<Twa so that the medical examination item is confirmed as 12B at the changed time. The final 12A becomes the final time of the medical examination item 12B since as for the time when an appointment is possible under the condition after the medical examination completion time of the confirmed 12B, Twb is the time at, and after, the completion time of the final patient id7 and this value is confirmed.

In FIG. 4, as for the process corresponding to "<e-id insertion>" shown in FIG. 3, the time when only the medical examination item 12B confirms an appointment for the patient idn is delayed by the completion time of the final patient id5 of the queue of the medical examination item 12B by an integer times, or more, of the average medical examination time Tb per patient and, therefore, in this case the situation is shown where one empty id is inserted. Additionally in FIG. 4, when the confirmation of the appointment time and "<e-id insertion>" are completed, the time of each of the medical examination items when the next appointment is available is updated to the time shown immediately after the position of the vertical line indicated by an arrow of the queue of each of the medical examination items 12A to 12D. This time of the medical examination item 12B of FIG. 4 indicates the starting time of the empty id newly inserted in this time appointment process shown in FIG. 3 and represents the time immediately after the completion time of the final patient in other medical examination items (12A, 12C, 12D).

In the case that the queue 114Q set in the waiting queue means 114 is in the condition shown in FIG. 4, the first medical examination item is confirmed to be the medical examination item 12C of which the time when the next appointment is available is the earliest in the next implemented medical examination appointment process. When the time that the next appointment is available is updated under the condition after the completion time of this confirmed time, only the empty id of 12B causes the overlap of the medical examination time and, therefore, only 12B is updated to the time immediately after the completion time of the final patient so that the medical examination appointment order becomes 12D, 12B, and 12A. This empty id of 12B is utilized again for the next appointment.

Figure 6:
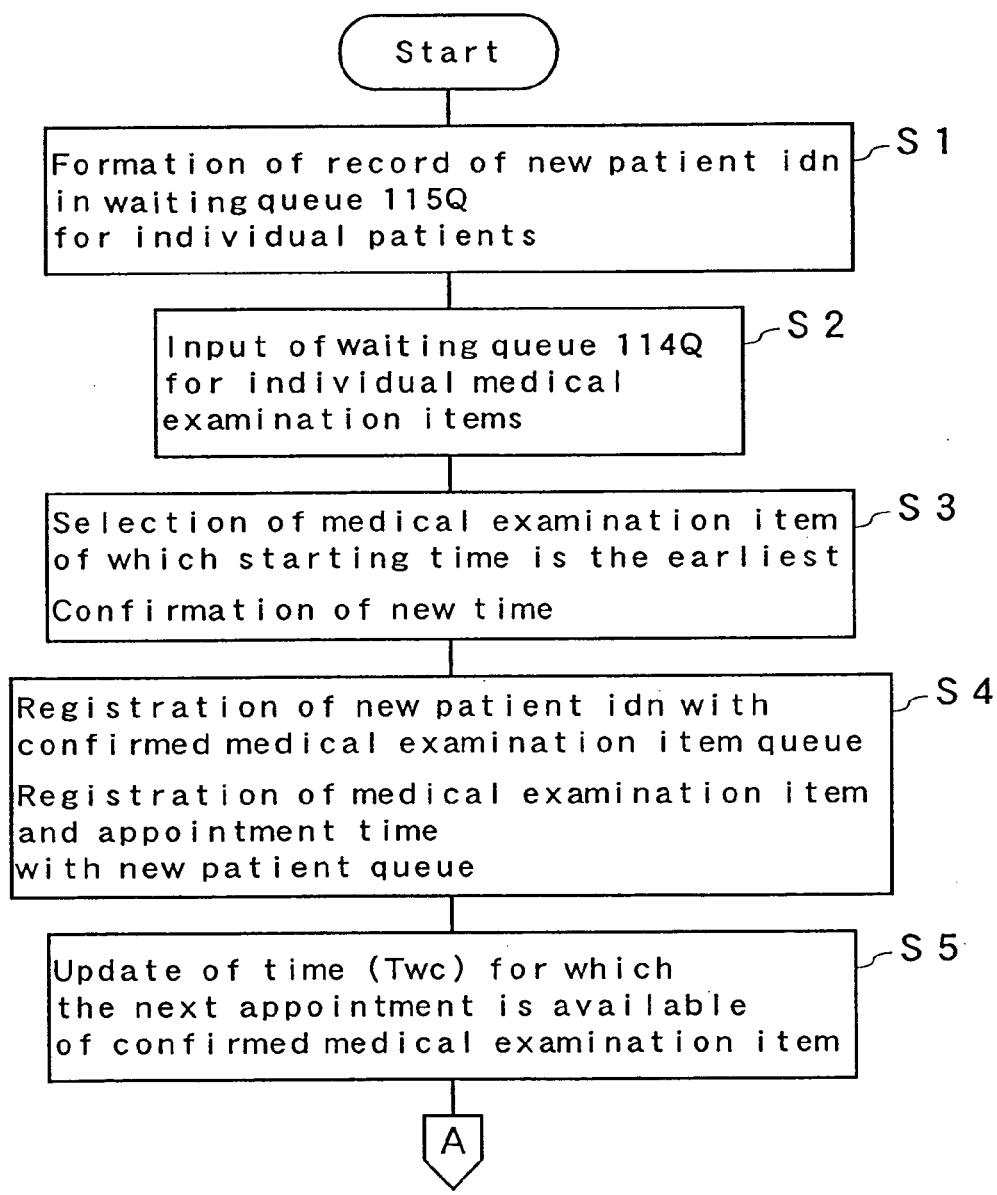
FIG. 6 is a flow chart showing the operation of the initial process for appointments and the configuration process for the first medical examination item according to the present embodiment.
Figure 7:
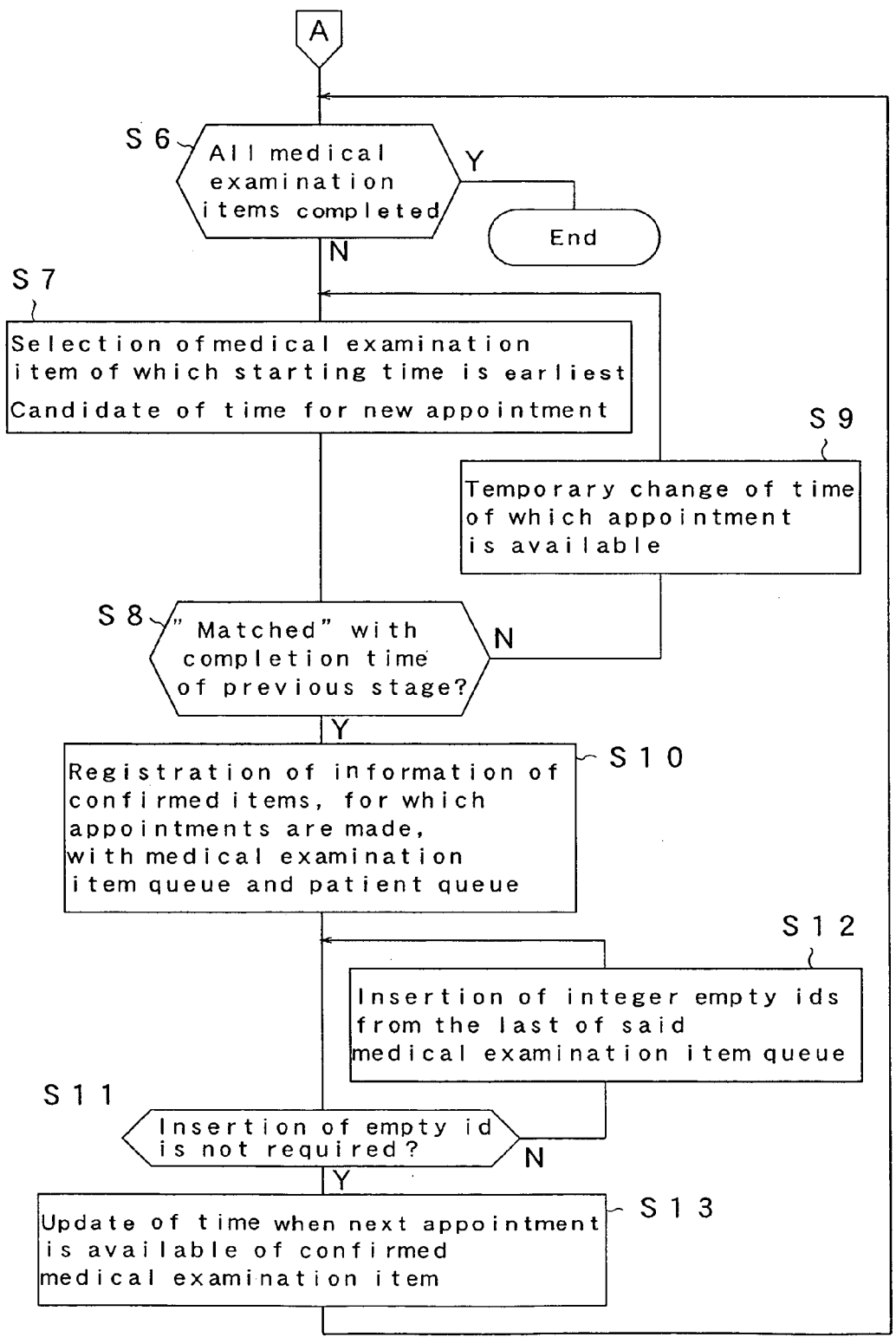
FIG. 7 is a flow chart showing the operation of the configuration process for the second medical examination item of the appointment process according to the present embodiment.

FIGS. 6 and 7 show flow charts of the case where a medical examination appointment process for a new patient (idn) is carried out by the scheduler 111 shown in FIG. 3 by utilizing the waiting queue 114Q for individual medical examination items shown in FIGS. 2 or 4 and the waiting queue 115Q for individual patients shown in FIG. 3. FIG. 6 shows the initial process and confirmation process for the first medical examination item while FIG. 7 shows the loop of the confirmation process of the second and later medical examination items.

In Step S1 of FIG. 6, first, the record of the new patient (idn) for whom this time appointment process is carried out is formed and added to the waiting queue 115Q for individual patients. Then, in Step S2 the waiting queue 114Q for individual medical examination items stored in a file format, or the like, at the appointment starting point as shown in FIG. 3 is inputted so as to be developed in the memory, or the like, and to carry out the preparation for the appointment process of this time.

In Step S3, in order to carry out a confirmation process for the first medical examination item, the medical examination item of which the starting time is the earliest from among the times (Twa to Twd) when the next appointment is available is decided by the comparison process between the times (Twa to Twd) for which the next appointment is available with respect to the entirety of the medical examination items (12A to 12D) of the waiting queue 114Q as shown in FIG. 2. In the waiting queue 114Q, the medical examination item 12C becomes the first medical examination appointment item and the time Twc when the next appointment is available becomes the appointment time.

In Step S4, a new patient id (idn) is registered with the time that is pointed out by the time (Twc) when the next appointment is possible after the confirmed medical examination item queue (12C). The new queue into which the first medical examination item and the starting time and finishing time are inputted is linked to the record of the new patient (idn) of the waiting queue 115Q formed in the first initialization process.

Next, in Step S5, the update processing of the time (Twc) for which the next appointment is available after the confirmed medical examination item queue (12C) is carried out. Here, in the case that the patient id (idn) is registered with the medical examination item queue (12C) which has been confirmed as the first item, no empty id exists for the medical examination item (12C) and, therefore, an update process is carried out with the time (Twc) when the next appointment is available immediately after the final patient id (id4) in this medical examination item queue (12C).

In FIG. 7, in the appointment process for the new patient (idn) of this time, the second and later medical examination items are confirmed. First, since there is a case where there is only one medical examination item, completion determination of the medical examination item is initially carried out in Step S6 and, in the case that all of the medical examination items have been confirmed, the appointment process is completed.

Next, in Step S7, in order to carry out the confirmation process for the second medical examination item, the medical examination item of which the starting time is the earliest from among the times when the next appointment is available (Twa, Twb, Twd) is determined through the comparison process of the times (Twa, Twb, Twd) when the next appointment is available with respect to the entirety of the medical examination items (12A, 12B, 12D) wherein the waiting queue 114Q is unconfirmed as shown in FIG. 2. In the waiting queue 114Q shown in FIG. 2, the medical examination item 12D becomes the second medical examination appointment item so that the time Twd for which the next appointment is available becomes a candidate of the appointment time.

Next, a determination process is carried out concerning whether or not the medical examination item 12D, which becomes the candidate of the appointment time in Step S8 and which has the time Twd for which the next appointment is available, can be confirmed. This determination process determines if the medical examination can be carried out without physically overlapping, in elapsed time, the appointment time which has been confirmed at the previous stage (in this case, after the completion time of the appointment (idn) for receiving the medical examination of the first medical examination appointment item 12C) and, in the case that the times do not physically overlap, it is determined to be "matched" so that the confirmation process is carried out. The time Twd for which the next appointment is possible of the medical examination item 12D matches the appointment time (Twc) wherein the first medical examination appointment item 12C is confirmed and, therefore, the procedure advances to the confirmation process.

Here, in the case that it is not determined to be "matched", the process for returning to the candidate detection process is again carried out after the time for which the next appointment is available with respect to each of the entirety of the unconfirmed medical examination items is temporarily changed by adding the condition after the completion time of the appointment time confirmed at the previous stage in Step S9. The second medical examination item in the waiting queue 114Q shown in FIG. 2 is confirmed at 12D. In the case that the medical examination item for which the starting time is the earliest from among the times (Twa, Twb) for which the next appointment is available with respect to each of the unconfirmed medical examination items (12A, 12B) is scheduled to be the third medical examination appointment item, it is not determined to be "matched" when the time Twb for which the next appointment is available of the medical examination item 12B is scheduled to be an appointment time candidate. Therefore, the temporary update processing of the times (Twa, Twb) for which the next appointment is available is carried out resulting in Twb being shifted back one medical examination time.

On the other hand, in the case of the determination of "matched" in Step S10, confirming the medical examination item and medical examination appointment time carries out the registration process. This process is the same as the registration process of the first medical examination item shown in FIG. 6 wherein a new patient id (idn) is registered with the time pointed out by the time for which the next appointment is available for the confirmed medical examination item queue is registered and a new queue into which the second and later medical examination items and their starting times and completion times are inputted is linked with the record of the new patient (idn) of the waiting queue 115Q for individual patients formed at the first initialization process.

In the case that the time for which the next appointment is available has not been determined to be "matched" so as to be temporarily changed, and the time for which the next appointment is available is utilized, a physically vacant time is generated between the completion time of the appointment of the final patient in the original medical examination item queue and the time for which the next appointment is available. In order to effectively utilize this vacant time, it is determined whether or not the vacant time has the interval of an integer times, or more, of the average medical examination time of the medical examination item in Step 511. In the case that there is such an interval, an insertion process of the empty id is carried out in Step 512. The third medical examination appointment item, only, is not determined to be "matched" in the waiting queue 114Q shown in FIG. 2, only in the case that the time Twb for which the next appointment is available of medical examination item 12B is scheduled to be an appointment time candidate. Therefore, a temporary update process of the time (Twa, Twb) for which next appointment is available is carried out. Consequently, since Twb has been shifted back one medical examination time unit, the determination process where the insertion of the empty id is unnecessary becomes NG and the insertion process of one empty id becomes necessary only for the medical examination item 12B.

Then, finally, an update process of the time for which the next appointment is available corresponding to the nth (n is an integer of 2 or larger) medical examination item queue which is confirmed in Step S13 is carried out. Here, since one empty id exists in the medical examination item queue (12B) with which the patient id (idn) is registered only in the medical examination item queue (12B) confirmed as the third item, an empty id immediately after the patient id5 is allocated for the time (Twb) of which the next appointment is available for this medical examination item queue (12B). In addition, in the figure, in order to carry out an appointment process for the entirety of the medical examination items, after the completion determination of the leading medical examination item is carried out and the procedure is looped until the entirety of the medical examination items have been confirmed.

Figure 5:
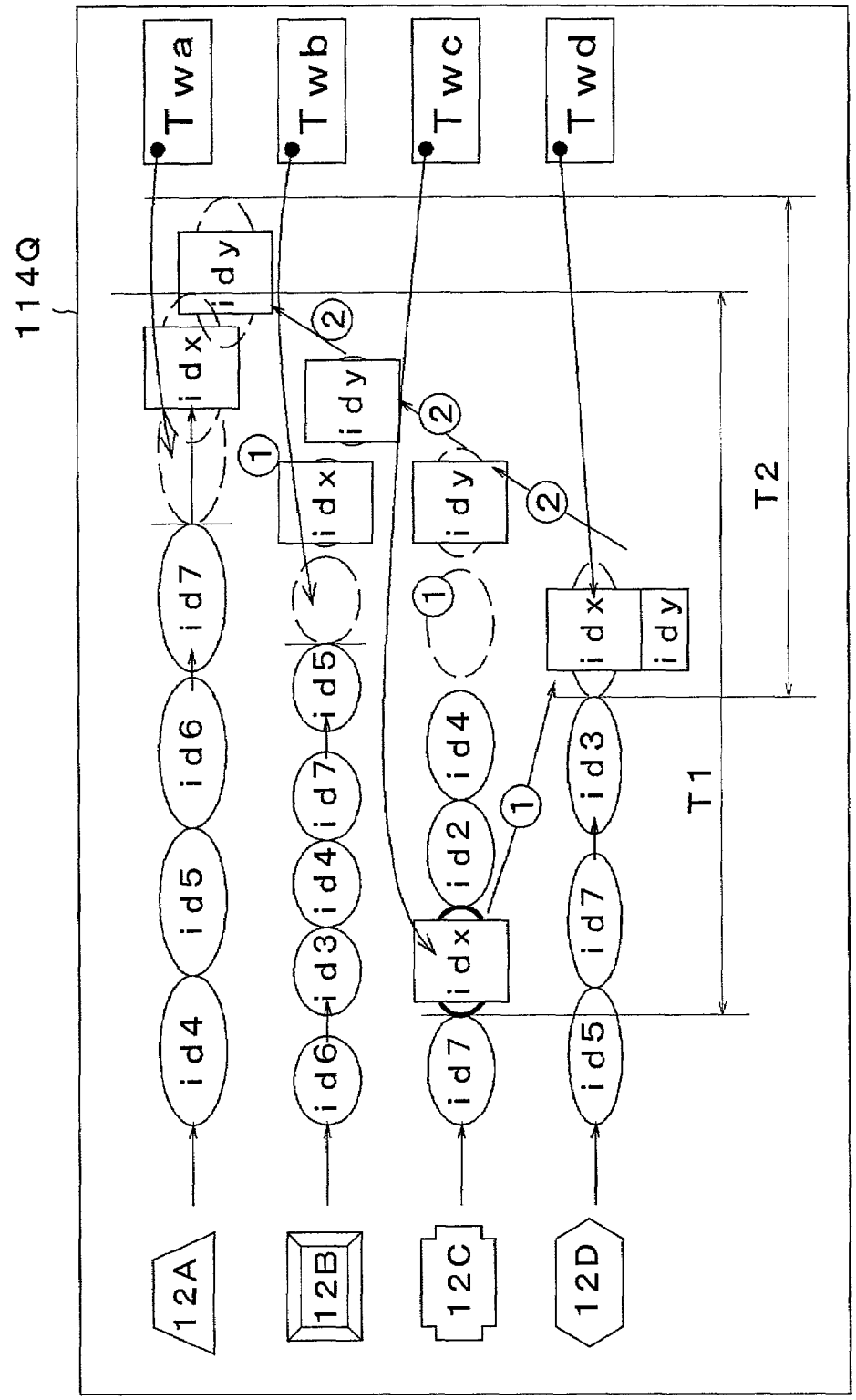
FIG. 5 is a diagram showing a process method for making an appointment by shortening the medical examination time even in the case that an isolated empty id occurs due to dispersion of the medical examination time among the medical examination items.

FIG. 5 illustrates the situation where isolated empty ids are replaced with void ids which cannot be utilized again so as to shorten the medical examination time by suppressing the effects thereof so that no patient who has scheduled an appointment has a long medical examination time due to the occurrence of isolated empty ids because of the dispersion of the time intervals of the average medical examination time Ta to Td of the medical examination items 12A to 12D shown in FIG. 2.

Now, in the case that the lead of the time for which the appointment is available is an isolated empty id for each patient, the maximum medical examination time is assumed to be set in advance at, for example, T0, or less. In FIG. 5 there is an isolated empty id at the second item of the queue of the medical examination item 12C and the time Twc for which the next appointment is available indicates the time of this leading empty id and the times Twd, Twb, Twa for which the next appointments are available for the other medical examination items 12D, 12B, 12A indicate the times immediately after the final patients id3, id5, id7, respectively. Therefore, the appointment process of the patient idx of this time has the order of 12C, 12D, 12B, and 12A. At this time, an empty id is inserted immediately after the final patient id5 of the medical examination item 12B in the route (1) according to the order and the medical examination time of the patient idx becomes T1 (>T0). This medical examination time T1 is equal to, or larger than, the medical examination time T0 that has been decided in advance and this appointment process is not confirmed because the first medical examination item 12C starts from the empty id. Therefore, this empty id is converted to a void id that cannot be utilized again so that the waiting time Twc of the medical examination item 12C is updated to the time immediately after the patient id4 that is the time for which the next appointment is available and the appointment process is repeated again. Then, an appointment is assumed to be scheduled for a new patient in the order of 12D, 12C, 12B, and 12A of idy the order becomes along the route (2) wherein empty ids are inserted immediately after the patient id4 of the medical examination item 12C and immediately after the patient id5 of the medical examination item 12B and the medical examination time is shortened to T2. In the case that this medical examination time T2 is the constant medical examination time T0, or less, and the first medical examination item 12D is not an empty id, the entire appointment process is confirmed in this route. (2) from these two.

Next, cancellation by the scheduler is described. When there is an application of cancellation of the medical examination appointment, in the case that there is not confirmation of the patient a constant time before the appointment time of the first medical examination item of the waiting queue for individual patients corresponding to the patient or in the case that there is an application for cancellation by the patient before that, then the waiting queue for individual patients for this patient is eliminated. Then, all of the patients who are queued in the waiting queue means 114 for individual medical examination items are moved to an empty queue so that reappointments for this time become possible. In addition, cancellation notices are given to the patients who have not yet scheduled appointments and appointment change notices are given to the patients who have already scheduled appointments.

Figure 8:
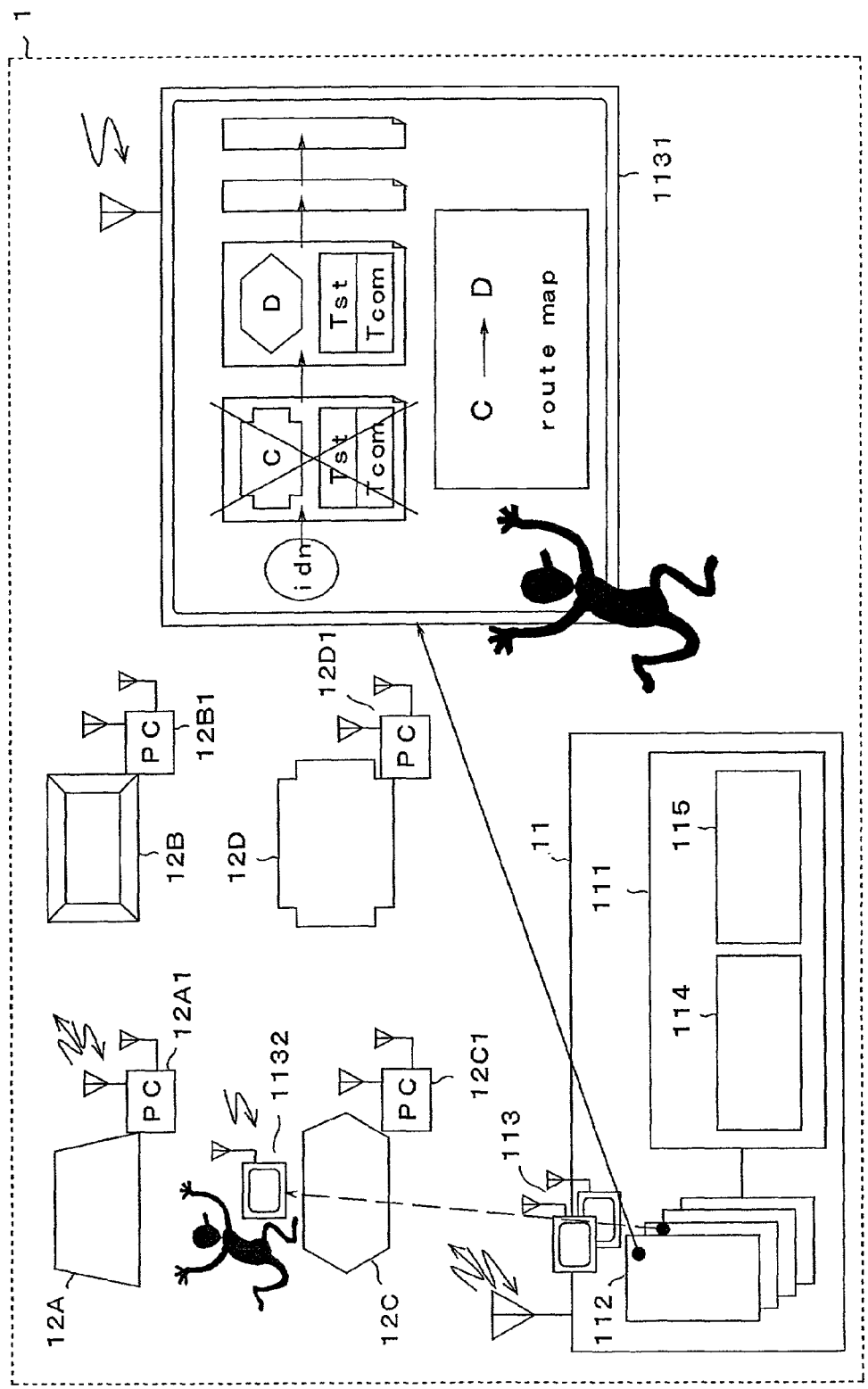
FIG. 8 is a diagram showing the situation of receiving each of the medical examination items in accordance with guidance information while carrying a wireless display device 1131 of FIG. 1 when visiting the actual site 1 of the medical examination shown in FIG. 1 after the patient idn carries out the appointment process.

FIG. 8 shows the situation where, after the patient idn shown in FIG. 3 performs the appointment process, the patient visits the actual site 1 of the medical examination at the appointment time, carries the wireless display device 1131 of FIG. 1 and receives each of the medical examination items in accordance with guidance information.

Figure 9:
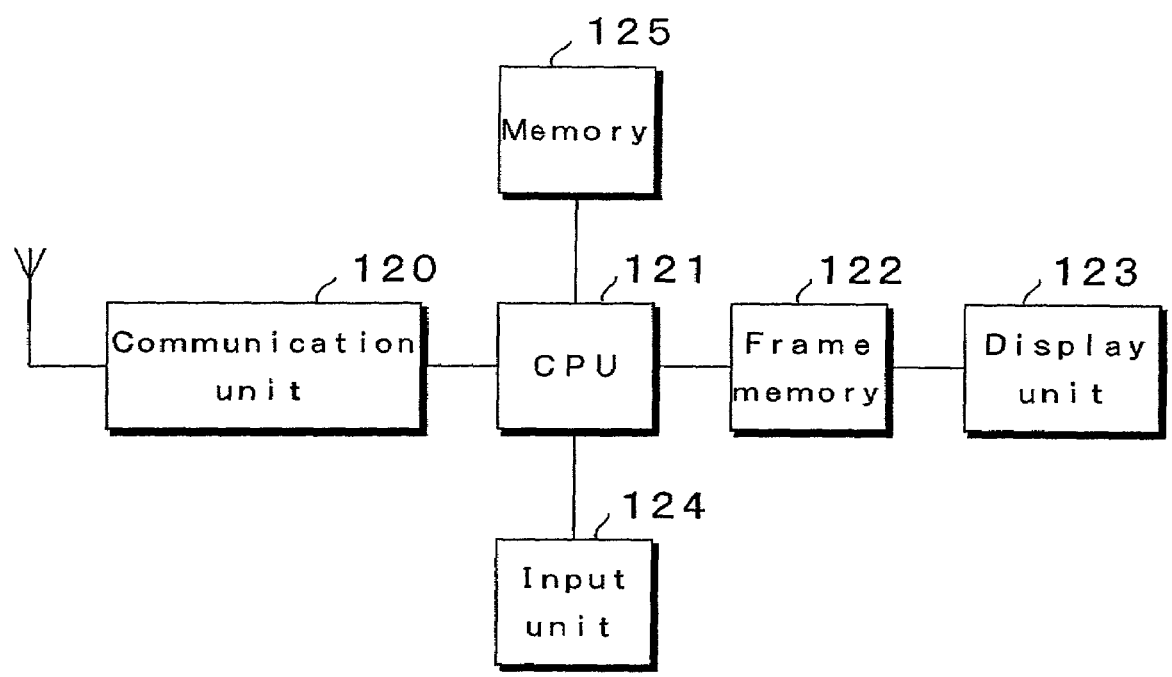
FIG. 9 is a block diagram showing one example of the wireless display device 113.

In FIG. 8 when the idn, which is an id of the patient, is registered at the reception, a wireless display device 1131 is delivered. FIG. 9 is a block diagram showing an example of the wireless display device. The wireless display device 113 is configured by including a communication unit 120, a CPU 121, a frame memory 122 and a display unit 123 such as of liquid crystal, or the like, an input unit 124, such as a touch panel, and a memory 125. The wireless display device 113 communicates with the server 11 and with the PCs 12A1 to 12D1 that are deposited in the vicinity of the medical examination items and displays a guide screen on the display unit 123. The PCs 12A1 to 12D1 also have communication means for communicating with the wireless display device 113 and the server 11 and the control means for outputting the completion of the medical examination of the patients.

Now, when a patient receives a wireless display device 1131, the wireless display device 1131 reads out the medical examination appointment contents of the corresponding idn of the waiting queue 115Q of the scheduler means 111 which have been registered at the reception and forms medical examination guidance information that indicates the route, the starting and finishing time and a map of the premises on one of the virtual realty displays 112. Then, the data are transmitted to the corresponding wireless display device 1131 so as to be displayed and the guidance information is updated whenever a medical examination item is completed.

Figure 10:
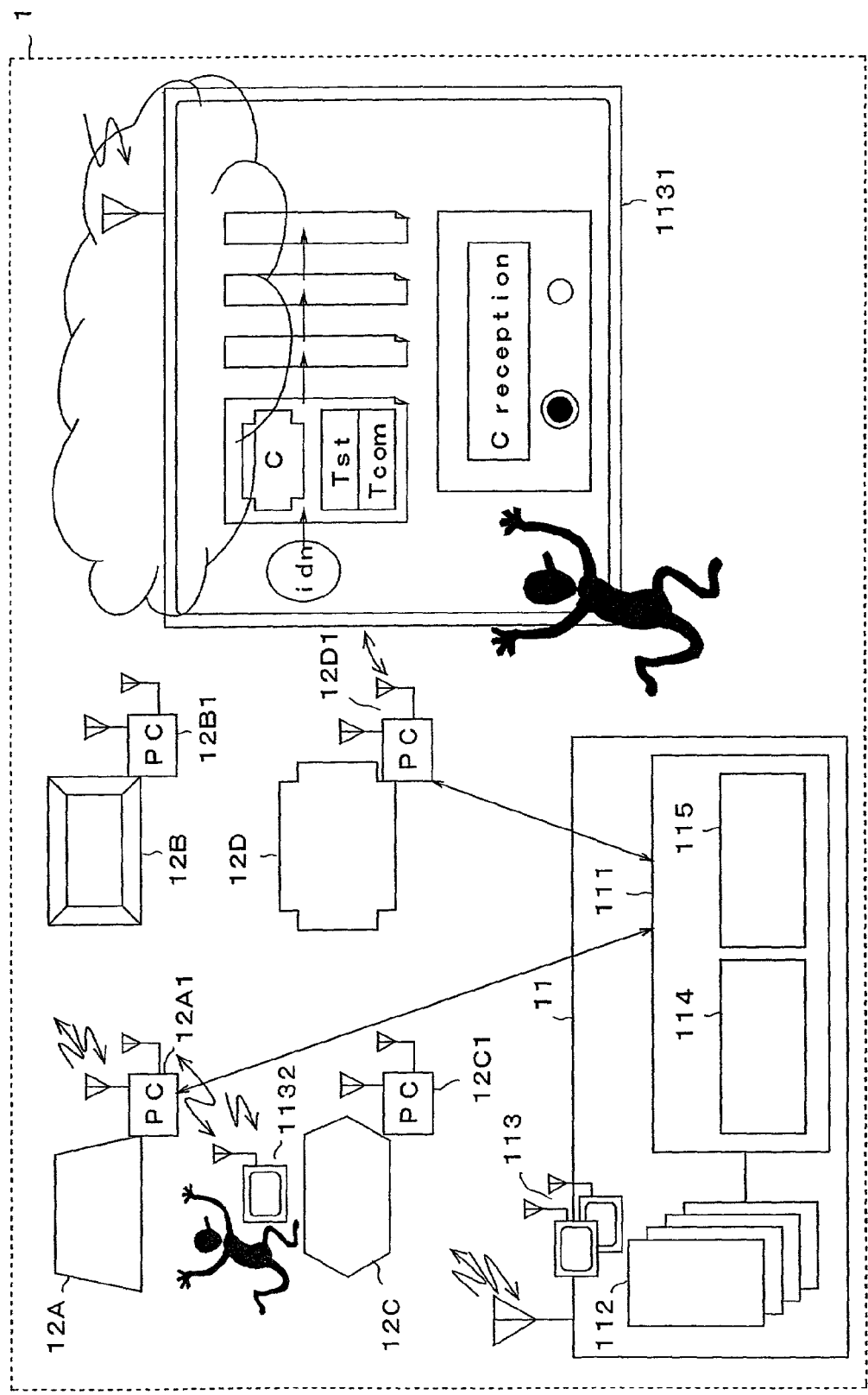
FIG. 10 is a diagram showing the situation of managing the arrival or the departure of the patients by PC 12A1 to 12D1 that has a wireless function installed for each of the medical examination items 12A to 12D through the communication with the wireless display devices 113 carried by the patients.

FIG. 10 shows the situation where the PCs 12A1 to 12D1 that are installed in the positions for each of the medical examination items 12A to 12D and which have a wireless function and a wireless display device 113 carried by a patient communicate regarding the arrival of a patient or the departure of a patient at the time of the completion of the medical examination.

In FIG. 10 the PCs 12A1 to 12D1 have two communication modes, the function of communicating with a wireless display device 113 only in the area around the entrance and the exit of the medical examination site with directionality for short distances and the function of communicating with the server 11. The PCs 12A1 to 12D1 download, from the server 11, and manage the waiting queue for individual patients of all of the patients who are present in the waiting queue for individual medical examination items and are present at the medical examination site 1. Accordingly, all of the patients who can arrive at the medical examination site from among the patients who have registered the ids at the reception are surveyed in a wireless manner and, when a response is returned from a wireless display device 113, an arrival notice is given to the server 11 so that an arrival icon is transmitted from the server 11 as a notice to the patient.

Figure 11:
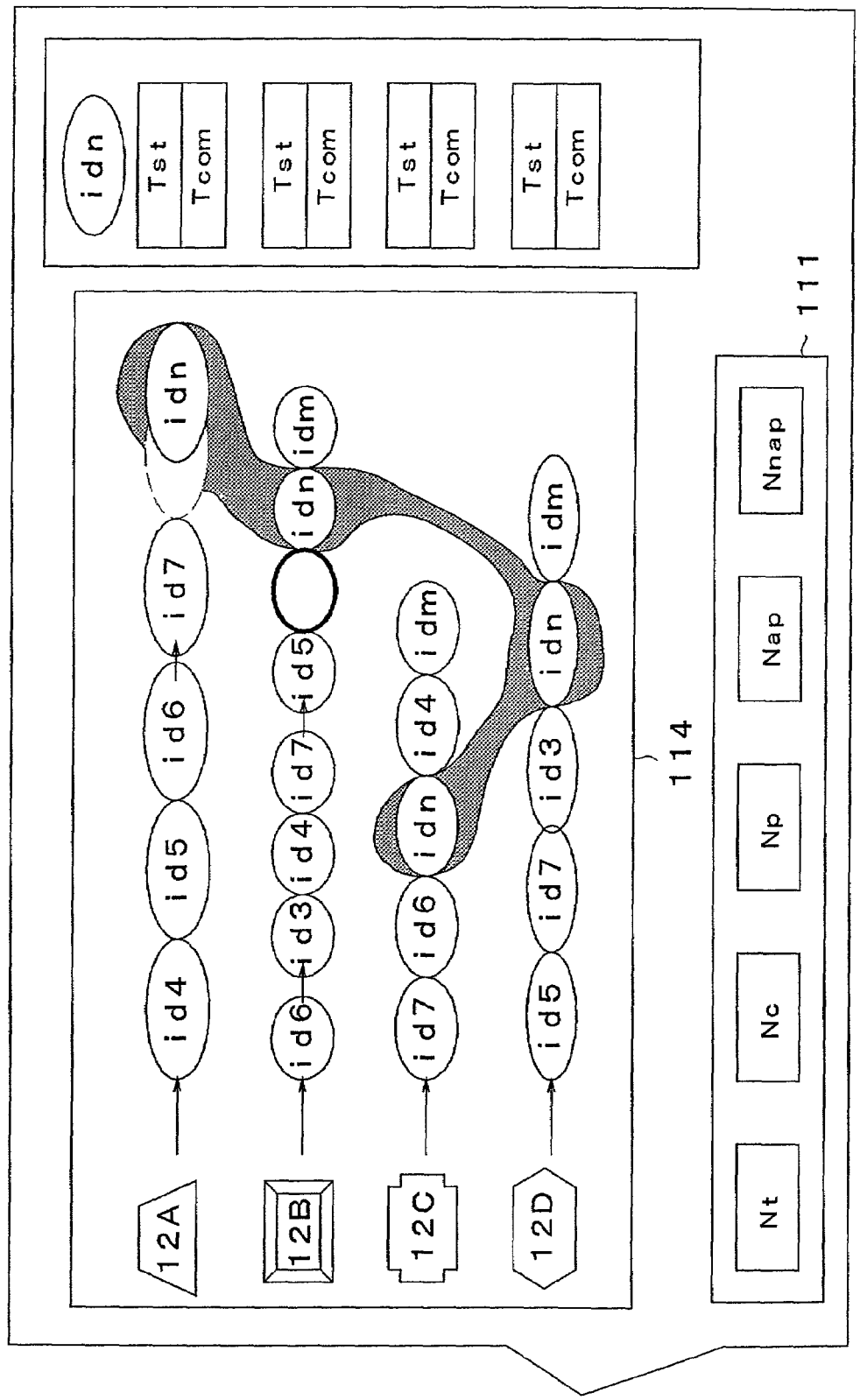
FIG. 11 is a diagram showing a screen for confirming the progress of the medical examination while staying at a work office 2 of each home or a farmer which is in places away from the site 1 of the medical examination as shown in FIG. 1 by connecting to the server 11 from the PC 21, 22 and 23 installed in the work office or a PC 31 or 32 installed at the home of the farmer via a network.

FIG. 11 shows a screen for confirming the status of progress of the medical examination, without patients leaving, through the connection from the PCs 21, 22, 23 installed in an office room 2 of a work office in a place apart from the medical examination site 1 as shown in FIG. 1 or the PCs 31, 32 installed at respective homes 3 of farmers to the server 11 via the network.

In FIG. 11, the status of progress shows the patients who are undergoing medical examination and the medical examination appointment list remaining in the waiting queue means 115 for individual medical examination items of the server 11 shown in FIG. 1. In the case that the patients who are confirming the status of progress have already scheduled an appointment, their own appointment queue is reversed so as to display the appointment times for individual medical examination items 12A to 12D of the patients. In the case that the patients who are confirming the status of progress have not yet scheduled an appointment, the times Twa to Twd for which the next appointments are available of the waiting queue means 114, which include conventional empty ids, are represented. The lower portion of FIG. 11 shows the situation where the total number of patients Nt who are to receive a medical examination on that day, the number of patients Nc who have already completed the medical examination and have been eliminated from the waiting queue means 114, the number of patients Np who are at present undergoing medical examination and who are marked, the number of patients Nap who have already scheduled an appointment and the number of patients Nnap who have not yet scheduled an appointment are displayed.

As described in detail above, according to the medical examination system of the present application, which has a simple configuration and portability, in the case of an on-site medical examination with the presupposition that the patients undergo medical examination during working hours, an appointment can be scheduled for an individual medical examination in a manner where the entire medical examination time becomes of the minimum grasping the status of progress of the medical examination of an office room or workplace where work is carried out. In addition, even in the case that the places, layout and the order for the medical examination have changed due to the installation conditions, guidance for the necessary medical examination order and for the medical examination place can be carried out based on the appointment conditions for individual patients by means of a wireless display device at the medical examination site. Accordingly, it becomes possible to provide a medical examination system wherein amount of time of interruption of work by the medical examination can be kept to a minimum and patients can undergo medical examination without becoming confused concerning the route of a medical examination at an unfamiliar site.

It is to be understood that although the present invention has been described with regard to preferred embodiments thereof, various other embodiments and variants may occur to those skilled in the art, which are within the scope and spirit of the invention, and such other embodiments and variants are intended to be covered by the following claims.

The text of Japanese priority application no. 2001-112387 filed Apr. 11, 2001 is hereby incorporated by reference.

What is claimed is:

1. A medical examination system for scheduling an appointment for patients comprising:
    a plurality of wireless display devices that have a display part and a communication part held by each patient waiting for a medical examination; and
    a server including a plurality of displays, said plurality of displays being capable of displaying guidance information including appointments included in a scheduler and displaying information from said respective wireless display devices, and a wireless communication means for communicating with said respective wireless display devices, wherein said scheduler includes:
    a waiting queue means for individual medical examination items for forming waiting queues for each of a plurality of medical examination items and sequentially queuing the medical examination appointments of the patients, and a waiting queue means for individual patients for forming waiting queues for each patient and sequentially queuing medical examination items for which appointments are scheduled,
    said scheduler includes means for scheduling a first appointment for a first medical examination of said medical examination items so that an available time to start said first medical examination on said medical examination items is calculated,
    said scheduler includes means for scheduling at least a second appointment for a second medical examination of said medical examination items so that an available time to start said second medical examination on said medical examination items is calculated after the first appointment which has been previously confirmed with respect to remaining queues of said waiting queue means for individual medical items; and
    said scheduler includes means for maintaining an unconfirmed state of an entire appointment process in case an interval between a starting time of the first appointment and a completion time of an appointment for a last medical examination item becomes at least equal to a predetermined amount of time and one of said medical examination items starts with an empty queue time period and means for changing the empty queue time period to a void queue time period that cannot be utilized again, and
    means for repeating an appointment process and means for confirming the entire appointment process when an interval between the starting time of the first appointment and the completion time of the appointment for said last medical examination item becomes less than the predetermined amount of time and one of said medical examination items starts with a non-empty queue time period,
    wherein said server includes means for forming information concerning medical examination guidance including an individual medical examination order, a starting time and an order of said medical examination items based on said waiting queue means for individual patients and said waiting queue means for medical examination items, on one of said plurality of displays of said server for respective patients, and
    wherein said wireless display devices display the waiting queues for the respective patient as a queue data structure and guidance relating to a medical examination route in a form of at least one of dynamic maps and directions to a next scheduled medical examination item appointment to individual patients via said wireless communication means of said server.

2. The medical examination system according to claim 1, wherein said server includes means for allowing a database of said server to be accessed from an external network.

3. A medical examination system for scheduling an appointment for patients comprising:
    a plurality of wireless display devices that have a display part and a communication part held by each patient waiting for a medical examination; and
    a server including a plurality of displays, said plurality of displays being capable of displaying guidance information including appointments included in a scheduler and displaying information from said respective wireless display devices, and a wireless communication means for communicating with said respective wireless display devices, wherein said scheduler includes:
    a waiting queue means for individual medical examination items for forming waiting queues for each of a plurality of medical examination items and sequentially queuing the medical examination appointments of the patients, and a waiting queue means for individual patients for forming waiting queues for each patient and sequentially queuing medical examination items for which appointments are scheduled,
    said scheduler includes means for scheduling a first appointment for a first medical examination of said medical examination items so that an available time to start said first medical examination on said medical examination items is calculated,
    said scheduler includes means for scheduling at least a second appointment for a second medical examination of said medical examination items so that an available time to start said second medical examination on said medical examination items is calculated after the first appointment which has been previously confirmed with respect to remaining queues of said waiting queue means for individual medical items, and
    said scheduler includes means for maintaining an unconfirmed state of an entire appointment process in case an interval between a starting time of the first appointment and a completion time of an appointment for a last medical examination item becomes at least equal to a predetermined amount of time and one of said medical examination items starts with an empty queue time period and means for changing the empty queue time period to a void queue time period that cannot be utilized again, and
    means for repeating an appointment process and means for confirming the entire appointment process when an interval between the starting time of the first appointment and the completion time of the appointment for said last medical examination item becomes less than the predetermined amount of time and one of said medical examination items starts with a non-empty queue time period, and
    said scheduler further includes means for determining that a completion time for an appointment for one of said medical examination items is delayed for at least an average time required for the medical examination on said one of said medical examination items and means for utilizing an empty queue time period in said waiting queue means for individual medical examination items so that a time for a next appointment is available for each of said medical examination items, said scheduler further includes means for representing a starting time as a leading queue when an empty queue time period exists within said queue and for representing a starting time when no empty queue time periods exist by the time immediately after the final patient completes a medical examination appointment so that the time is registered with said waiting queue means for individual patients and said waiting queue means for individual medical examination items by calculating the time so as to start from a time when an appointment is available in an earliest medical examination item, wherein said server includes means for forming information concerning medical examination guidance including an individual medical examination order, a starting time and an order of medical examination items based on said waiting queue means for individual patients and said waiting queue means for medical examination items, on one of said plurality of displays of said server for respective patients, and wherein said wireless display devices display the waiting queues for the respective patient as a queue data structure and guidance relating to a medical examination route in a form of at least one of dynamic maps and directions to a next scheduled medical examination item appointment to individual patients via said wireless communication means of said server.

4. The medical examination system according to claim 3, said medical examination system further comprises:

a personal computer installed in a medical examination site, wherein said personal computer comprises a communication means for communicating at close range with the wireless display device carried by a patient, a communication means for communicating with said server and a control means for outputting information relating to at least one of arrival of the patient and completion of the medical examination of the patient.

5. The medical examination system according to claim 3, wherein said server includes means for allowing a database of said server to be accessed from an external network.

6. A method for scheduling an appointment of a medical examination for patients, said method comprising the steps of:

providing a plurality of wireless display devices, having a display part and a communication part, to a patient waiting for a the medical examination;

providing a server including a plurality of displays, the plurality of displays being capable of displaying guidance information including appointments included in a scheduler and displaying information from the respective wireless display devices, a wireless communication means for communicating with the respective wireless display devices, forming waiting queues for individual medical examination items, and forming waiting queues for each patient, scheduling a first appointment for a first medical examination of the medical examination items so that an available time to start the first medical examination on the medical examination items is calculated; and scheduling at least a second appointment for a second medical examination of the medical examination items so that an available time to start the second medical examination on the medical examination items is calculated after the first appointment which has been previously confirmed with respect to remaining queues of the waiting queues for individual medical items;

maintaining an unconfirmed state of an entire appointment process in case an interval between a starting time of the first appointment and a completion time of an appointment for a last medical examination item becomes at least equal to a predetermined amount of time and one of said medical examination items starts with an empty queue time period and means for changing the empty queue time period to a void queue time period that cannot be utilized again, and repeating an appointment process and means for confirming the entire appointment process when an interval between the starting time of the first appointment and the completion time of the appointment for said last medical examination item becomes less than the predetermined amount of time and one of said medical examination items starts with a non-empty queue time period;

providing information concerning medical examination guidance including an individual medical examination order, a starting time and an order of the medical examination items based on the waiting queue for individual patients and the waiting queue for medical examination items, on one of the plurality of displays of the server for respective patients; and displaying the waiting queues for the respective patient as a queue data structure and guidance relating to a medical examination route in a form of at least one of dynamic maps and directions to a next scheduled medical examination item appointment to individual patients from the server.

* * * * *